US009358219B2

(12) United States Patent
Davis

(10) Patent No.: US 9,358,219 B2
(45) Date of Patent: Jun. 7, 2016

(54) PHARMACEUTICAL COMPOSITION

(75) Inventor: Adrian Francis Davis, Dorking Surrey (GB)

(73) Assignee: Futura Medical Developments Limited, Surrey (GB)

(*) Notice: Subject to any disclaimer, the term of this patent is extended or adjusted under 35 U.S.C. 154(b) by 331 days.

(21) Appl. No.: 13/497,920

(22) PCT Filed: Nov. 10, 2010

(86) PCT No.: PCT/GB2010/051870
§ 371 (c)(1),
(2), (4) Date: May 8, 2012

(87) PCT Pub. No.: WO2011/058351
PCT Pub. Date: May 19, 2011

(65) Prior Publication Data
US 2012/0248142 A1    Oct. 4, 2012

(30) Foreign Application Priority Data

Nov. 10, 2009 (GB) .................................. 0919650.2

(51) Int. Cl.
*A61K 9/06* (2006.01)
*A61K 31/245* (2006.01)
*A61K 9/00* (2006.01)
*A61K 47/02* (2006.01)
*A61K 47/24* (2006.01)
*A61K 47/34* (2006.01)

(52) U.S. Cl.
CPC ............. *A61K 31/245* (2013.01); *A61K 9/0014* (2013.01); *A61K 9/0034* (2013.01); *A61K 47/02* (2013.01); *A61K 47/24* (2013.01); *A61K 47/34* (2013.01)

(58) Field of Classification Search
None
See application file for complete search history.

(56) References Cited

U.S. PATENT DOCUMENTS

| 5,631,248 | A | * | 5/1997 | Davis et al. ................... 514/179 |
| 6,136,332 | A | * | 10/2000 | Grollier ................. A61K 8/585 |
| | | | | 424/404 |
| 6,325,990 | B1 | * | 12/2001 | Laurent .......................... 424/45 |
| 2002/0006435 | A1 | * | 1/2002 | Samuels et al. ............... 424/449 |
| 2005/0209319 | A1 | * | 9/2005 | Cundy .......................... 514/484 |
| 2005/0281750 | A1 | | 12/2005 | Willcox et al. |
| 2006/0147383 | A1 | * | 7/2006 | Mallard et al. .................. 424/45 |
| 2007/0135379 | A1 | | 6/2007 | Mallard et al. |
| 2007/0248548 | A1 | * | 10/2007 | Blondino et al. ............... 424/44 |
| 2008/0194528 | A1 | | 8/2008 | Barthez et al. |
| 2008/0292560 | A1 | | 11/2008 | Tamarkin et al. |
| 2009/0093547 | A1 | | 4/2009 | Corbitt et al. |

OTHER PUBLICATIONS

Y Cui. "Enhanced Release of Lidocaine from Supersaturated Solutions of Lidocaine in a Pressure Sensitive Adhesive." PhD Thesis, Ohio State University, 2003, pp. i-xvi and 1-196.*
Univar Corporation. "A Comprehensive Portfolio of Personal Care Products from Univar." http://www.univar.com/~/media/PDFs/US%20Corp%20Region%20PDFs/PC/Univar%20Personal%20Care%20Product%20List%20by%20INCI.ashx, accessed Aug. 18, 2015, 15 printed pages.*

* cited by examiner

*Primary Examiner* — Isaac Shomer
(74) *Attorney, Agent, or Firm* — Stites & Harbison, PLLC; Terry L. Wright

(57) ABSTRACT

A pharmaceutical composition comprises an active ingredient dissolved in an essentially non-aqueous carrier system comprising volatile and non-volatile components, in which the volatile component comprises a volatile non-solvent for the active ingredient and a volatile solvation additive for the non-solvent and the non-volatile component comprises a non-volatile non-solvent and optionally a non-volatile solvent for the active ingredient, the volatile and non-volatile non-solvents comprising silicone fluids of respectively different viscosity.

13 Claims, 1 Drawing Sheet

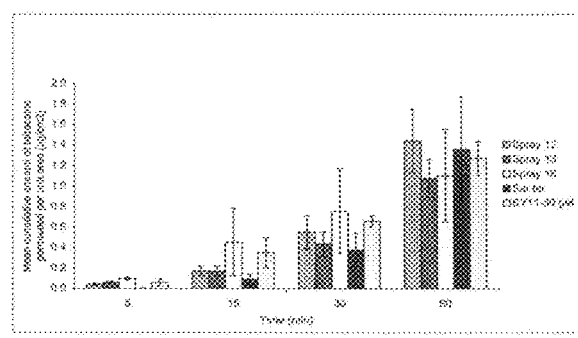

Tetracaine flux from silicone spray 12, 13 and 16 (3.47 to 10.23 to 16.61

Tetracaine flux from silicone spray 12, 13 and 16 (3.47 to 10.23 to 16.61 supersaturation), an experimental BY11-30 gel and a high dose saturated tetracaine control.

PHARMACEUTICAL COMPOSITION

This invention relates to pharmaceutical compositions for topical application to a part of the human body, especially but not exclusively for the treatment of premature ejaculation.

Premature ejaculation (PE) is a condition which occurs in approximately 20-25% of the male population, and is the most common sexual dysfunction in men aged 40 years or less. The condition is classified either as "lifelong PE" or "acquired PE" and in each case is broadly characterised as ejaculation with minimal sexual stimulation either before, on or shortly after penetration during sexual intercourse takes place and before the person concerned wishes it to happen, with negative personal consequences. Typically, the duration of intercourse lasts for less than one or two minutes, rather than the normal eight to ten minutes or longer for males without the condition. When present, the condition has a psychosocial impact on both the male and his partner, the psychosocial effect if anything tending to exacerbate the condition if left untreated. The causes of premature ejaculation are unknown, although lifelong PE is regarded as likely to have organic causes while acquired PE is generally considered as psychological. Research has shown that most men with premature ejaculation do not seek assistance from their physician and, of those that do, most are dissatisfied with the result.

Possible treatments include manual procedures such as the stop-start or squeeze-pause technique carried out by the female partner and the use of desensitising creams for the male. Orally-administered antidepressant compositions have also been tried. In particular, compositions comprising topical anaesthetics have been subject to extensive trial and it has been reported that EMLA cream containing 2.5% lidocaine and 2.5% prilocalne, applied 30 minutes before sexual contact takes place, was considered as highly efficacious by most subjects, the intravaginal ejaculation latency time (IVELT) increasing from 1.47 to 8.45 minutes in one trial, with a placebo resulting in an increase from 1.67 to 1.95 minutes. The effect of dose of lidocaine and prilocalne from EMLA cream was studied by varying the contact time of the cream over 20-30-45 minutes and comparing with placebo. In the 20 minute group, IVELT increased to 6.71 minutes with no change in placebo group. In the 30 minutes group, IVELT increased to 8.7 minutes in four subjects; however the remaining six subjects and all ten subjects in the 45 minute group had erection loss because of numbness. Although this, and similar studies, proves the principle of treating premature ejaculation with a topical local anaesthetic the long time before onset of effect and the lack of control of intensity of effect are not satisfactory from a user perspective. Thus, clearly, it is necessary to administer the local anaesthetic in a dose which is absorbed rapidly yet in a controlled manner to achieve loss of sensitivity without inducing numbness in the penis.

Other treatments which have been for PE include the use of PDE5 inhibitors and psychological/behavioural therapy.

As a result of clinical experience with topical local anaesthetic gels for premature ejaculation and consumer research/feedback from sufferers, the following requirements have been identified as desirable:
  rapid onset of action;
  short duration of action, typically from five to ten minutes;
  appropriate intensity of action (reduced sensitivity but not numbness);
  safety for the partner; and
  appropriate aesthetics and ergonomics for satisfactory consumer acceptance, including packaging;

Of the above, the first three are dose requirements, specifically for control of onset, duration and intensity of activity.

In the overall design of formulations which will be acceptable, it is necessary to consider not only the therapeutic quality in terms of efficacy, also taking account of plasma levels and systemic safety levels, but also consumer acceptability in terms of local tolerance of the active ingredient and of other components of the formulation, ease of use and aesthetic considerations including viscosity and skin sensation. Pharmaceutical requirements in terms of stability, shelf life and physical stability are also important.

U.S. Pat. No. 6,325,990 discloses a composition for spraying on the skin and comprising a lipophilic active compound, including analgesics such as lidocaine, from 0.5-25% by weight of a silicone-based adhesive polymer composition; from 0-25% by weight of an absorption promoter; from 25-95% by weight of a volatile solvent comprising volatile silicones; and from 0.5-50% by weight of a pressurised propellant gas. Preferably, the volatile silicones represent from 50-85% by weight of the composition. Additionally, the compositions include up to 25% of a volatile solvent such as ethanol.

US2006/0147383 discloses a pharmaceutically-active agent such as lidocaine hydrochloride contained in an alcoholic vehicle including at least one volatile silicone and a non-volatile oily phase, for administration by spraying. The volatile silicone is present at between 25 and 95% by weight of the composition. Preferably, an alcohol is also present as a solvent, at a concentration of at least 15%, preferably at least 25% of ethanol.

US2007/0135379 discloses a pharmaceutical composition in the form of a gel having an active ingredient, for example, an anaesthetic, a silicone agent comprising at least one organopolysiloxane elastomer and optionally a solvent such as ethanol or other lower alcohol. The elastomer has viscoelastic properties and a concentration from 1-20%, more particularly from 5-10%, by weight relative to the total composition.

US2008/0194528 discloses a viscoelastic organopolysiloxane having viscoelastic properties in a composition particularly for treatment of psoriasis, the active ingredient being at least one vitamin D-derived compound. The elastomer may be formulated in a volatile or non-volatile silicone oil.

It is an object of the present invention to provide topical pharmaceutical compositions for the treatment of premature ejaculation, in which the active ingredient is contained in a non-aqueous carrier system preferably for administration as a spray, and which contains the active ingredient dissolved in a blend of volatile and non-volatile solvents whereby, in use and as the volatile solvent evaporates, the active ingredient becomes supersaturated in the residual phase. Depending on the degree of supersaturation achieved, and thus the penetration rate of the anaesthetic into the surface of the glans penis, and on the total dose of local anaesthetic applied, rapid onset and appropriate intensity and duration of local anaesthetic effect may be achieved.

In one aspect, the present invention provides a topical pharmaceutical composition, the composition comprising an active ingredient dissolved in an essentially non-aqueous carrier system comprising volatile and non-volatile components, in which the volatile component comprises a volatile non-solvent for the active ingredient and a volatile solvation additive for the non-solvent and the non-volatile component comprises a non-volatile non-solvent and optionally a non-volatile solvent for the active ingredient, the volatile and non-volatile non-solvents comprising silicone fluids of respectively different molecular weight and viscosity.

The non-volatile solvent components are preferably mutually totally miscible and the composition is preferably single-phase.

Compositions according to the invention preferably include the active ingredient in solution at a concentration close to the saturation level so that, on application to the penis or other body part and as the volatile component, especially the silicone fluid, evaporates, the residual phase becomes super-saturated whereby there is a continuing driving force for absorption of an effective amount of active ingredient as the residual phase is absorbed through the skin and as the volatile component continues to evaporate, the effect being essentially localised to the body part or skin zone in question without the absorption creating a significant accumulation of active ingredient in the systemic circulation. Depending upon the dose of the active ingredient and the amount of the combined miscible non-volatile component and the active ingredient solubility in the non-volatile component (thus the degree of supersaturation), formulations having rapid onset and appropriate intensity and duration of activity may be realised.

For use in inducing numbness, the dose of the active ingredient would normally be higher than for use in premature ejaculation treatment.

It has surprisingly been found that the presence of the solvation additive, even in relatively minor concentrations compared with the volatile silicone fluid, has the effect not only of dissolving the active ingredient but also of enhancing the solvating power of the volatile silicone fluid, resulting in the ability to increase the amount of active ingredient in the composition without encountering problems in precipitation of active ingredient in use, and without requiring the presence of higher concentrations of solvating additive, which may be undesirable in terms of unpleasant burning skin sensations, for example. Desirably, depending on the dose amount of active ingredient, the concentration of solvation additive should be less than 10% by weight, more preferably less than 5% by weight, based on the total composition.

The active ingredient may be any compound or mixture of compounds known to be effective when administered topically, subject to solubility properties in the carrier system. Local anaesthetics, provided that they have the desired solubility properties, represent a class of active ingredients suitable for use in the present invention but other active ingredients in topical compositions may also be used. Where the active ingredient is a local anaesthetic, the composition may be used for the treatment of premature ejaculation, especially acquired PE, but may also be used in accordance with a further object of the invention, which is to provide topical compositions for applications where local and short-term skin desensitisation or numbness is required, for example to make injections more acceptable to children.

Compositions according to the invention are characterised by having rapid onset and appropriate intensity and duration of activity, this latter requirement being achieved by high absolute bioavailability of relatively low doses and the normal pharmacokinetic clearance of the local anaesthetic or other active ingredient.

It is, in general, preferable that compositions according to the invention for anaesthetic purposes have the following properties:
that on spray application to the skin (e.g. of the penis) a supersaturated solution is provided which is stable for up to 20-30 minutes, which thus requires preferably that:
the local anaesthetic is totally in solution in the full spray formulation
the spray formulation is a single phase
the components of the spray formulation remain as a single phase upon loss of volatiles, and also
that the drug remains in supersaturated solution and that upon rapid loss of the volatile silicone,
the volatile solvation additive, non-volatile solvent and non-volatile silicone remain as a single phase in all foreseeable combinations.

In compositions according to the present invention, the terms "solvent" and "non-solvent" are relative rather than absolute. The terms "volatile" and "non-volatile" are also relative rather than absolute. Expressed in functional terminology, the volatile solvent or solvation additive should be an effective solvent for the active ingredient, to provide a completely dissolved concentration of active ingredient consistent with dose requirements in the formulation as a whole, as well as enhancing the solvating power of the non-solvent. The volatile silicone fluid should have sufficient volatility to enable it to evaporate rapidly from the formulation on application to the body, for example the penis, the external skin temperature of which is typically approximately 30-31° C., at ambient temperatures of up to approximately 40° C., but more usually 20-25° C. in temperate climates, thereby driving the active ingredient towards supersaturation in the residual phase remaining as the volatile solvent component (i.e. silicone and additive) evaporates, while retaining the composition as a single phase. The volatile solvation additive enhances the solvating power of the otherwise relatively poorly-solvating volatile silicone fluid which in turn acts to limit the amount of volatile solvation additive required, since the additive is preferably used in moderate amounts in the composition to prevent unpleasant sensations such as skin burning.

The optional non-volatile solvent component may comprise an emollient agent to promote or enhance the skin absorption properties of the composition. Suitable non-volatile solvents for this purpose include isopropyl palmitate and isopropyl myristate but other similarly-acting compound's, especially ester compounds, may alternatively be used, as will be understood by the skilled person. Selection of such agents is based on active ingredient solubility and miscibility with the other vehicle components. The optional non-volatile agent allows for adjustment of the active ingredient in the non-volatile residual phase. In this way, extremely high degrees of supersaturation, which would tend to nucleate and recrystallise immediately with no therapeutic benefit, may be reduced to achieve the 20-30 minutes stability required.

In formulations according to the present invention, the volatile solvation additive preferably comprises a lower alcohol containing up to five carbon atoms. Suitable alcohols include linear and branched chain aliphatic alcohols such as isopropyl alcohol and n-butanol although ethanol is preferred. Again, selection of the volatile solvent alcohol is based on active ingredient solubility and miscibility with the other vehicle components but the solvent should have sufficient solvating power to enhance the solvating power of the volatile silicone fluid and to maintain a single phase, without crystallisation, as the volatile component evaporates in use and the composition becomes supersaturated. Formulations according to the invention are essentially free of water, excepting the approximately 4% water which is azeotropically present in normal commercially-available ethanol, for example.

The active ingredient which may be used in formulations according to the invention may include lidocaine, prilocalne, benzocaine, etidocaine and tetracaine, the choice being based on considerations of potency and skin penetration ability. Tetracaine, also known as amethocaine, is the preferred local anaesthetic in that it has a high ratio of skin penetration (flux, μg/cm²/time) to potency (μM or μg/cm³), this being indicative of the potential for topical efficacy. Tetracaine, 2(dimethylamino)ethyl-4-(butylamino)benzoate, is a basic compound available either as the free base or as the hydrochloride salt. Compositions containing tetracaine preferably have a pH in the range 5 to 8, higher pHs favouring solubility in, and thus penetration across, the stratum corneum skin barrier. For use in the formulations of the present invention, tetracaine free base is used. Lidocaine free base, although less potent than tetracaine, may nevertheless be preferred as an anaesthetic compound already accepted for topical use in many markets. Lidocaine hydrochloride is unsuitable for use in the present compositions because of its extremely low solubility with respect to the dose of lidocaine required.

For the treatment of premature ejaculation, the concentration of tetracaine as an example of a suitable local anaesthetic should be sufficient to deliver up to 50 μg/cm², for example, from 6-30 μg/cm², per 10 minutes to the glans penis in a unit dosage amount of from 200 to 400 mg, preferably around 300 mg per dose, equivalent to approximately 6 mg of composition per square centimeter of the glans penis. This would be realised by a tetracaine concentration of from 0.1-0.5% up to 1.0% by weight, equivalent to an amount of from 0.3-1.5 up to 2.5 mg of tetracaine in absolute terms, given the assumed requirements in the model being considered. For lidocaine, the preferred dose is from 7.5 to 12.5% by weight, for example 10% by weight of the formulation.

The volatile silicone fluid for use in compositions according to the present invention typically comprises a linear and/or cyclic silicone. By volatile is meant a liquid having a measurable vapour pressure at 25° C. and a flash point less than 100° C. Preferably, the volatile silicone has a boiling point than 250° C. and a viscosity in the range of about 0.5-5 cSt, preferably about 0.6-2 cSt. Suitable volatile linear silicones include those having the formula $(CH_3)_3SiO[(CH_3)_2SiO]_xSi(CH_3)_3$ in which x is 0 to 5, preferably 0 to 3, for example 0 or 1. Suitable volatile silicones are available from Dow Corning as Q7-9180 silicone fluids according to the above formula; the fluid where x is 0 has a viscosity of 0.65 cSt and the fluid where x is 1 has a viscosity of 1.0 cSt. Cyclic volatile silicones have the general formula $[Si-O(CH_3)_2]_n$ where n is 3 to 8, preferably 4 to 6. Suitable cyclic silicones are available from Dow Corning, identified as D4, octamethylcycloquadrosiloxane and D5, decamethylcyclopentasiloxane. For example, D4 and/or D5 cyclic silicones may be used in compositions according to the invention although linear silicones are generally preferred. For use in treatment of premature ejaculation, where rapid onset of effect is caught, the highly volatile silicone fluid 0.65 cSt is preferred.

The non-volatile non-solvent preferably comprises a silicone oil. By non-volatile is meant a liquid oil that does not have a significant vapour pressure at 25° and a flash point greater than 100° C. with typical viscosity values between about 20 to 50,000 cSt, preferably 20 to 12,500 cSt. Suitable silicone oils are available from Dow Corning as Q7-9120 silicone fluids of various viscosities, depending on molecular weight. It has been found that the solubility of the active ingredient decreases with increasing molecular weight, a decrease in solubility being useful in maintaining high activity states in the residual phase of compositions according to the present invention, but an increase in molecular weight has an adverse effect in decreasing the miscibility with the non-volatile solvent ester component, where present.

Compositions according to the present invention for use in the treatment of premature ejaculation may contain, in percentages by weight, from 0.1 to 15%, preferably from 0.1 to 12%, of local anaesthetic active ingredient, for example tetracaine at up to 1.0% or lidocaine at up to 15%, for example from 7.5 to 12.5%, preferably 10%; from 2 to 15%, preferably 3.5 to 10%, of volatile solvation additive; from 65 to 90%, preferably from 70 to 90%, of volatile silicone fluid and from 1.0 to 20, preferably 1.5 to 15%, of non-volatile silicone fluid. Optionally, the compositions include a non-volatile solvent as an emollient or thickening agent at a concentration up to 10%, preferably up to 8%, by weight.

Where the active ingredient comprises tetracaine, the volatile solvation additive is preferably present at a concentration of 7.5 to 10%; the volatile silicone fluid is preferably present at a concentration of 75 to 90%; the non-volatile silicone fluid is preferably present at a concentration of 1.5 to 15% and the non-volatile solvent at a concentration of 0 to 2.5%, the total non-volatile component preferably amounting to 2.0 to 15%, all percentages being expressed by weight of the total composition before use.

Where the active ingredient comprises lidocaine, the volatile solvation additive is preferably present at a concentration of 3.5 to 4.5%; the volatile silicone fluid is preferably present at a concentration of 65 to 80%, more preferably 68 to 77.5%; the non-volatile silicone fluid is preferably present at a concentration of 2.0 to 10%, more preferably 2.0 to 7.5% and the non-volatile solvent is preferably present at a concentration of 2.0 to 10%, the total non-volatile component preferably amounting to 7.5 to 20%, more preferably 9.0 to 18%, all percentages again being expressed by weight of the total composition before use.

Compositions according to the invention may be formulated for application as a gel or a cream or as a spray formulation. Spray formulations are preferably propellant free and are provided in a pumpable container, preferably one providing a metered dose.

Table 1 below provides formulations for exemplary compositions according to the invention containing tetracaine as active ingredient and, for comparative purposes, that of an experimental silicone gel and a high dose saturated tetracaine control.

TABLE 1

Silicone formulations and saturated control solution.

| Ingredient | Spray 12, 0.25% | Spray 13, 0.25% | Spray 16, 0.25% | Spray 18, 0.1% | Spray 19, 0.5% | BY11-030 gel, 0.25% | Saturated control |
|---|---|---|---|---|---|---|---|
| Tetracaine base | 0.25 | 0.25 | 0.25 | 0.10 | 0.50 | 0.25 | >2.4 |
| Ethanol | 8.50 | 8.50 | 8.50 | 8.50 | 8.50 | 10.00 | 0.00 |
| Silicone fluid 0.65 CST | 76.25 | 77.75 | 87.75 | 89.12 | 80.80 | 66.75 | 0.00 |
| Silicone fluid 12500 CST | 13.50 | 13.50 | 3.00 | 1.94 | 9.18 | 0.00 | 0.00 |
| IPP | 1.50 | 0.00 | 0.50 | 0.34 | 1.02 | 0.00 | 0.00 |
| BY11-030 | 0.00 | 0.00 | 0.00 | | | 20.00 | 0.00 |
| Water | 0.00 | 0.00 | 0.00 | | | 3.00 | 0.00 |
| Propylene | 0.00 | 0.00 | 0.00 | | | 0.00 | <97.6 |

TABLE 1-continued

Silicone formulations and saturated control solution.

| Ingredient | Spray 12, 0.25% | Spray 13, 0.25% | Spray 16, 0.25% | Spray 18, 0.1% | Spray 19, 0.5% | BY11-030 gel, 0.25% | Saturated control |
|---|---|---|---|---|---|---|---|
| glycol | | | | | | | |
| Tetracaine solubility in the residual phase | 0.48 | 0.18 | 0.43 | | | Unknown | >2.4 |
| Supersaturation | 3.47 | 10.23 | 16.61 | | | Unknown | 1 |

IPP: isopropylpalmitate

The formulations shown in Table 1 were investigated for their skin absorption properties in vitro across human epidermal membrane. Accompanying FIG. 1 shows tetracaine flux ($\mu g/cm^2$) at times up to one hour, compared with the experimental gel and the control in propylene glycol. It is to be seen that flux increases with time and also with the degree of supersaturation in the residual phase, at least at early times. At later times, there is less distinction between the effect of the different formulations but, for use in treatment of premature ejaculation, the flux at early times is more significant.

Local anaesthetics, including tetracaine, are also used to provide peripheral anaesthesia of the skin. For example, Ametop Gel (Tetracaine 4%) is indicated for prevention of pain following venepuncture or venous cannulation. For this indication, profound anaesthesia is required and also, depending on clinical logistics, anaesthesia over a longer period of time may be required. Current formulations, for example Ametop Gel, are required to be used under occlusion to increase skin penetration of the active ingredient but even so, onset time is slow, at over 30 minutes, and local anaesthetic effect is only partial.

Silicone-based formulations according to the present invention have potential to provide peripheral anaesthesia of the skin subject to suitable dose and solubility requirements. For example, using the same input rates (from 6-30 $\mu g/cm^2$ up to 50 $\mu g/cm^2$ per 10 minutes) but modified for a 60 minutes duration equates to concentrations of 0.6-5.0% of active ingredient, for example tetracaine. In practice, because a more profound analgesia is required for this indication then for PE, doses in the top end of the range, for example 2.5-5.0%, are preferred.

In another aspect, therefore, the present invention provides a composition for use in inducing peripheral anaesthesia of the skin and containing, in percentages by weight, from 1 to 7.5% of local anaesthetic active ingredient; from 60 to 80% of silicone volatile non-solvent; from 10 to 20% of volatile solvation additive; from 2.0 to 5.0% of non-volatile solvent; and from 5 to 15% of non-volatile non-solvent.

Such higher doses require adjustment of the ratios of the solvents to achieve two objectives:
1) Increase in drug solubility in the total formulation (volatiles and non-volatiles) to ensure complete drug solubility.
2) Increase in drug solubility in the non-volatile residual phase to ensure that appropriate degrees of supersaturation are achieved. Very high degrees of supersaturation lead to rapid crystallisation and reduction in skin penetration.

Table 2 shows some exemplary formulations of higher dose tetracaine-containing local anaesthetic formulations.

TABLE 2

High dose (HD) tetracaine formulations according to the invention.

| Ingredient | Spray HD T1 | Spray HD T2 | Spray HD T3 | Spray, HD T4 | Spray HD T5 |
|---|---|---|---|---|---|
| Tetracaine base | 5.00 | 5.00 | 2.50 | 2.50 | 2.50 |
| Ethanol | 17.0 | 17.0 | 17.0 | 17.0 | 17.0 |
| Silicone fluid 0.65 CST | 68.00 | 68.00 | 68.00 | 68.00 | 68.00 |
| Silicone fluid 12500 CST | 12.00 | 11.25 | 12.75 | 12.00 | 11.25 |
| IPM | 3.00 | 3.75 | 2.25 | 3.00 | 3.75 |
| total | 105.00 | 105.00 | 102.50 | 102.50 | 102.50 |
| Tetracaine solubility in the no-volatile phase | 1.40% | 2.50% | 0.80% | 1.40% | 2.50% |
| Supersaturation | 22.67 | 12.69 | 20.83 | 11.62 | 6.51 |

Table 3 shows some exemplary spray formulations of lidocaine free base-containing local anaesthetic formulations.

TABLE 3

| Ingredient | Spray 1 10% non-volatile (25:75 IPP:silicone fluid 20) | Spray 2 10% non-volatile (50:50 IPP:silicone fluid 20) | Spray 3 10% non-volatile (75:25 IPP:silicone fluid 20) | Spray 4 15% non-volatile (50:50 IPP:silicone fluid 20) | Spray 5 20% non-volatile (50:50 IPP:silicone fluid 20) | Spray 6 20% non-volatile (75:25 IPP:silicone fluid 20) |
|---|---|---|---|---|---|---|
| Lidocaine | 10.00 | 10.00 | 10.00 | 10.00 | 10.00 | 10.00 |
| Ethanol | 4.05 | 4.05 | 4.05 | 3.825 | 3.6 | 3.6 |
| Silicone fluid 0.65 CST | 76.95 | 76.95 | 76.95 | 72.675 | 68.4 | 68.4 |
| IPP | 2.25 | 4.50 | 6.75 | 6.75 | 9.00 | 13.50 |
| Silicone fluid 20 CST | 6.75 | 4.50 | 2.25 | 6.75 | 9.00 | 4.50 |
| Total | 100.0 | 100.0 | 100.0 | 100.0 | 100.0 | 100.00 |

The invention claimed is:

1. A pharmaceutical composition comprising an active ingredient dissolved in an essentially non-aqueous carrier system comprising volatile and non-volatile components, in which the volatile component comprises a volatile non-solvent for the active ingredient and a volatile solvation additive for the non-solvent and the non-volatile component comprises a non-volatile non-solvent and optionally a non-volatile solvent for the active ingredient, the volatile and non-volatile non-solvents comprising silicone fluids of respectively different viscosity,
   wherein the pharmaceutical composition contains, in percentages by weight, from 0.1 to 15% of local anaesthetic as the active ingredient; from 2 to 15% of the volatile solvation additive; from 65 to 90% of a silicone volatile non-solvent; from 1.0 to 20% of the non-volatile non-solvent and optionally up to 10% of the non-volatile solvent,
   wherein the volatile solvation additive comprises a lower alcohol containing up to five carbon atoms, the volatile non-solvent comprises a linear and/or cyclic silicone, and the non-volatile non-solvent comprises a silicone oil,
   wherein the active ingredient has a concentration close to the saturation level whereby, in use on application to the body and as the volatile components evaporate, the residual phase becomes super-saturated to provide a continuing driving force for absorption of an effective amount of active ingredient through the skin as the volatile components continue to evaporate,
   wherein the non-volatile solvent and non-volatile non-solvent are totally miscible, including in the residual phase, when the non-volatile solvent is present in the composition,
   and wherein the composition is single-phase, including in the residual phase.

2. A composition according to claim 1, in which the non-volatile solvent component comprises an emollient agent to promote or enhance the skin absorption properties of the composition.

3. A composition according to claim 1, in which the linear silicone has the formula $(CH_3)_3SiO[(CH_3)_2SiO]_xSi(CH_3)_3$ in which x is 0 to 5 and the cyclic silicone has the general formula $[Si—O(CH_3)_2]n$ where n is 3 to 8.

4. A composition according to claim 1, in which the concentration of active ingredient is from 0.1 to 1.0%; of volatile solvation additive is from 7.5 to 10%; of volatile non-solvent is from 75 to 90%; of non-volatile non-solvent is from 1.5 to 15% and of non-volatile solvent is 0 to 2.5%.

5. A composition according to claim 1, in which the active ingredient comprises tetracaine.

6. A composition according to claim 1, in which the active ingredient comprises lidocaine free base.

7. A composition according to claim 1, formulated as a gel or cream.

8. A composition according to claim 1, formulated as a spray.

9. A composition according to claim 8, packaged in a propellant-free pumpable container.

10. A composition according to claim 1, wherein the non-volatile solvent is selected from isopropyl myristate and isopropyl palmitate.

11. A composition according to claim 5, wherein the tetracaine is a tetracaine free base.

12. A composition according to claim 9, wherein the propellant-free pumpable container provides a metered unit dose.

13. A method of inducing peripheral anaesthesia, comprising administering to the skin of a subject a composition comprising an active ingredient dissolved in an essentially non-aqueous carrier system comprising volatile and non-volatile components, in which the volatile component comprises a volatile non-solvent for the active ingredient and a volatile solvation additive for the non-solvent and the non-volatile component comprises a non-volatile non-solvent and optionally a non-volatile solvent for the active ingredient, the volatile and non-volatile non-solvents comprising silicone fluids of respectively different viscosity,
   wherein the composition contains, in percentages by weight, from 0.1 to 15% of local anaesthetic as the active ingredient; from 2 to 15% of the volatile solvation additive; from 65 to 90% of a silicone volatile non-solvent; from 1.0 to 20% of the non-volatile non-solvent and optionally up to 10% of the non-volatile solvent,
   wherein the volatile solvation additive comprises a lower alcohol containing up to five carbon atoms, the volatile non-solvent comprises a linear and/or cyclic silicone, and the non-volatile non-solvent comprises a silicone oil,
   wherein the active ingredient has a concentration close to the saturation level whereby, in use on application to the body and as the components evaporate, the residual phase becomes super-saturated to provide a continuing driving force for absorption of an effective amount of active ingredient through the skin as the components continue to evaporate,
   wherein the non-volatile solvent and non-volatile non-solvent are totally miscible, including in the residual phase, when the non-volatile solvent is present in the composition,
   and wherein the composition is single-phase, including in the residual phase.

* * * * *